United States Patent [19]

Hiraga et al.

[11] 4,334,914
[45] Jun. 15, 1982

[54] BENZOATE DERIVATIVE, METHOD OF PREPARING THE SAME AND USE THEREOF AS A HERBICIDE

[75] Inventors: Kunikazu Hiraga, Izumi; Katsumasa Okawa, Kawachinagano; Kenichi Ikeda, Toyonaka; Masanori Hikawa, Kawachinagano, all of Japan

[73] Assignee: Nihon Nohyaku Co., Ltd., Tokyo, Japan

[21] Appl. No.: 234,104

[22] Filed: Feb. 12, 1981

[30] Foreign Application Priority Data

Feb. 13, 1980 [JP] Japan .................................. 55/16347

[51] Int. Cl.³ .................... A01N 37/36; A01N 37/00; C07C 153/11; C07C 69/76
[52] U.S. Cl. ........................................ 71/100; 71/108; 260/455 R; 560/65
[58] Field of Search ...................... 260/455 R; 560/65; 71/100, 108

[56] References Cited

U.S. PATENT DOCUMENTS 3,953,489  4/1976  Tamura et al. ................. 260/455 R
3,957,852  5/1976  Fujikawa et al. ..................... 560/65

OTHER PUBLICATIONS

Noller, Textbook of Organic Chemistry, W. B. Saunders Company, Philadelphia, 1958, p. 128.

Primary Examiner—Henry R. Jiles
Attorney, Agent, or Firm—Cushman, Darby & Cushman

[57] ABSTRACT

Novel benzoate derivatives having a powerful herbicidal effect on various weeds grown in paddy fields, upland fields, and other places have been found out, which are represented by the formula

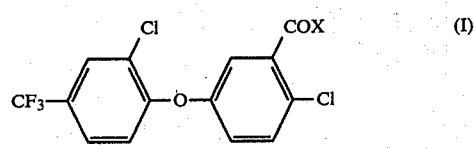

wherein X is —SR, —O$(CH_2CH_2O)_n$R, —OCH$_2$CH$_2$SR,

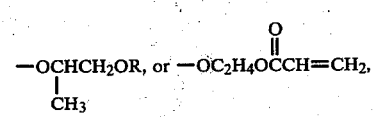

herein R being lower alkyl and n being an integer of 1 to 3.

16 Claims, No Drawings

BENZOATE DERIVATIVE, METHOD OF PREPARING THE SAME AND USE THEREOF AS A HERBICIDE

The present invention relates to novel compounds and more particularly to novel benzoate derivatives having a herbicidal effect.

The invention provides benzoate derivatives represented by the formula

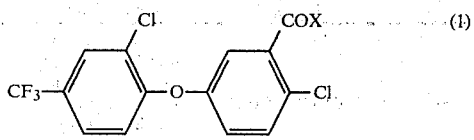

wherein, X is $-SR$, $-O\text{-}(CH_2CH_2O)_nR$, $-OCH_2CH_2SR$,

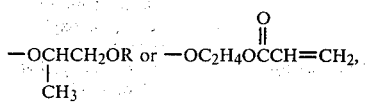

herein R being lower alkyl and n being an integer of 1 to 3, and it also provides a process for producing these benzoate derivatives and usage thereof.

The compounds represented by formular (1) above are especially useful as herbicides.

The compounds of formula (1) are novel, i.e., unreported in the literature. The reaction path of a typical process for synthesizing these compounds is schematically shown below:

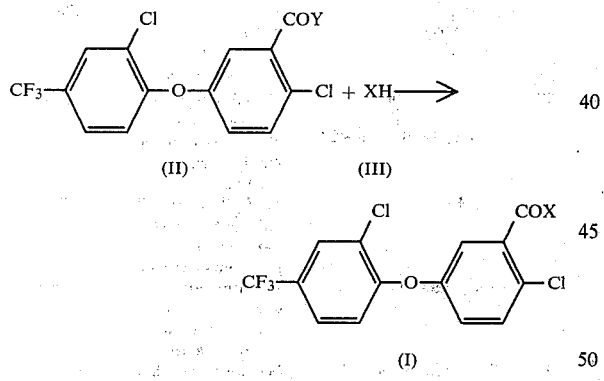

In this equation, Y is halogen atom and X is as defined above.

Thus, the compounds of formula (I) can be obtained by reacting compounds represented by formula (II) with compounds represented by formula (III) in an inert solvent in the presence or absence of a base.

The inert solvent used in the reactions may be any of those not seriously hindering this type reaction; for example, the possible solvents are aromatic hydrocarbons such as benzene, toluene, and xylene; ethers such as ethyl ether, tetrahydrofuran, and dioxane; ketones such as acetone, methyl ethyl ketone, and cyclohexanone; lower fatty acid esters such as ethyl acetate; lower fatty acid amides such as dimethylformamide and dimethylacetamide; dimethylsulfoxide; and pyridine. These solvents may be used separately or in combination.

The bases which can be used for the above reaction include inorganic bases such as, for example, sodium carbonate, sodium hydroxide, potassium carbonate, sodium hydrogencarbonate, and potassium hydrogencarbonate; and organic bases such as, for example, pyridine, trimethylamine, triethylamine, diethylaniline, and 1,8-diazabicyclo-[5,4,0]-7-undecene.

The above reaction can proceed at a temperature of 0° to about 200° C., preferably at a temperature appropriately chosen within the range of from room temperature to 150° C.

The reaction between compounds (II) and (III) in the reaction path can be carried out by using the reactants in equimolar ratio, but it is unobjectionable to use either one in slight excess.

After completion of the reaction, the objective material can be obtained through customary treatments of the reaction products. For example, it is accomplished by extracting the objective material from the reaction products with a suitable solvent, washing and drying the extract, and removing the solvent.

The compounds represented by formula (II) used as the starting material are novel ones unreported in the literature. The compound (Y is chlorine) can be synthesized by reacting 2-chloro-5-(2-chloro-4-trifluoromethylphenoxy)-benzoic acid with a chlorinating agent such as thionylchloride, phosphorus trichloride, or phosphorus oxychloride; or by reacting 5-(2-chloro-4-trifluoromethylphenoxy)-2-sulfobenzoic acid with phosphorus pentachloride.

Further, 5-(2-chloro-4-trifluromethylphenoxy)-2-sulfobenzoic acid (m.p. 300° C. or more) can be synthesized through the following reaction path:

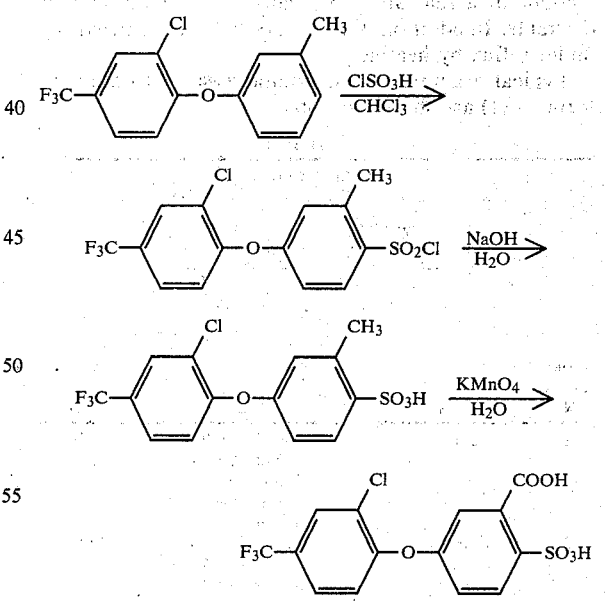

The compounds represented by the formula

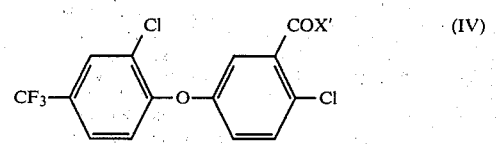

which is included in formula (I), wherein X' is
—O—(CH$_2$CH$_2$O)$_{\overline{n}}$R or $$-\underset{\underset{CH_3}{|}}{O}CHCH_2OR.$$

herein R being lower alkyl and n being an integer of 1 to 3, can be synthesized also through the following reaction path schematically shown:

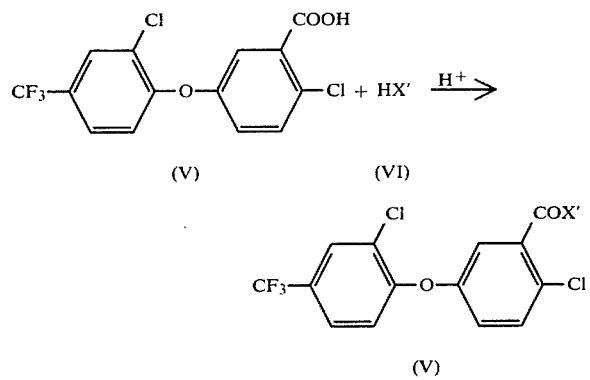

in this equation, X' is as defined above.

That is, a compound represented by formula (IV) can be obtained by reacting the compound represented by formula (V) with a compound represented by formula (VI) in the presence of an acid such as sulfuric acid, hydrochloric acid, or p-toluenesulfonic acid.

Although the reaction proceeds when the amount ratio of both reactants is equimolar, the use of an excess amount of a reactant represented by formula (VI) is desirable. In addition, the reaction is better carried out under reflux by heating.

Typical examples of the compounds represented by formula (1) are shown in Table 1.

TABLE 1

In the formula

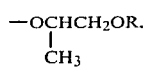

| Compound No. | X | Compound name | Refractive index $n^D$ (°C.) |
|---|---|---|---|
| 1 | —SCH$_3$ | s-Methyl-2-chloro-5-(2-chloro-4-trifluoromethyl-phenoxy)benzo-thioate | 1.5720 (28°) |
| 2 | —SC$_2$H$_5$ | s-Ethyl-2-chloro-5-(2-chloro-4-trifluoromethyl-phenoxy)benzo-thioate | 1.5612 (25°) |
| 3 | —SC$_3$H$_7$(n) | s-(n)-Propyl-2-chloro-5-(2-chloro-4-trifluoromethyl-phenoxy)benzo-thioate | 1.5662 (25°) |
| 4 | —OC$_2$H$_4$OCH$_3$ | Methoxyethyl-2-chloro-5-(2-chloro-4-trifluoromethyl-phenoxy)benzoate | 1.5321 (25°) |
| 5 | —O—C$_2$H$_4$OC$_2$H$_5$ | Ethoxyethyl-2-chloro-5-(2-chloro-4-trifluoromethyl-phenoxy)benzoate | 1.5272 (25°) |
| 6 | —OC$_2$H$_4$OC$_3$H$_7$(n) | (n)-Propoxyethyl-2-chloro-5-(2-chloro-4-trifluoromethyl-phenoxy)benzoate | 1.5218 (25°) |
| 7 | —O(C$_2$H$_4$O)$_2$CH$_3$ | Methoxyethoxyethyl-2-chloro-5-(2-chloro-4-trifluoromethyl-phenoxy)benzoate | 1.5270 (23°) |
| 8 | —O(C$_2$H$_4$O)$_2$C$_2$H$_5$ | Ethoxyethoxyethyl-2-chloro-5-(2-chloro-4-trifluoromethyl-phenoxy)benzoate | 1.5210 (25°) |
| 9 | —O(C$_2$H$_4$O)$_3$CH$_3$ | Methoxyethoxyethoxyethyl-2-chloro-5-(2-chloro-4-trifluoromethyl-phenoxy)benzoate | 1.5210 (25°) |
| 10 | —O(C$_2$H$_4$O)$_3$C$_2$H$_5$ | Ethoxyethoxyethoxyethyl-2-chloro-5-(2-chloro-4-trifluoromethyl-phenoxy)benzoate | 1.5175 (28°) |
| 11 | —OCHCH$_2$OCH$_3$<br>        \|<br>       CH$_3$ | 2-Methoxy-1-methyl-ethyl-2-chloro-5-(2-chloro-4-trifluoromethyl-phenoxy)benzoate | 1.5270 (28°) |
| 12 | —OC$_2$H$_4$OCCH=CH$_2$<br>          ‖<br>          O | Acryloyloxyethyl-2-chloro-5-(2-chloro-4-trifluoromethylphenoxy)-benzoate | 1.5340 (25°) |
| 13 | OC$_2$H$_4$SCH$_3$ | Methylthioethyl-2-chloro-5-(2-chloro-4-trifluoromethyl-phenoxy)benzoate | 1.5538 (25°) |
| 14 | OC$_2$H$_4$SC$_2$H$_5$ | Ethylthioethyl-2-chloro-5-(2-chloro-4-trifluoromethyl-phenoxy)benzoate | 1.5500 (23°) |
| 15 | OC$_2$H$_4$SC$_3$H$_7$(i) | Isopropylthioethyl-2-chloro-5-(2-chloro-4-trifluoromethylphenoxy)benzoate | 1.5434 (25°) |

The compounds represented by formula (1) shown above have herbicidal activity against typical strongly injurious weeds including; those known as strongly injurious paddy field weeds, for example, barnyard grass (*Echinochloa Crusgalli Beauv*, an annula gramineous weeds), umbrella plant (*Cyperus difformis L.*, an annual cyperaceous weeds), bulrush (*Scirpus juncoides Roxb.* var. hotarui ohwi., an annual cyperaceous weeds), Arrowhead (*Sagittaria pygmaea Miq.*, a perennial weeds of Alismataceae family), monochoria (*Monochoria vaginalis Presl*, an annual weeds of Pontederiaceae family); and those known as strongly injurious upland field weeds, for example, barnyard grass (above-mentioned), large crabgrass (*Digitaria adscendcus Henr.*, an annual gramineous weeds), Redroot pigweed (*Amaranthus viridis L.*, an annual weeds of Amaranthaceae family), mugwort (*Artemisia princeps Pamp.*, a perennial composite weeds), and umbrella sedge (*Cyperus iria L.*, an annula cyperaceous weeds). These compounds also have similar herbicidal activity against a variety of other grass weeds or broad-leaved weeds. Having herbicidal effect on weeds when used either before or after emergence of weeds, these compound are useful as a pre-emergence herbicide as well as a post-emergence herbicide to the weed. The compounds can also be used as a selective herbicide for applying before or after transplanting of crops, in a definite dosage and at a definite time for treatment. Thus, herbicidal compositions of the compounds can be used for various applications according to the herbicidal action of the active ingredients. When the compounds are used as a selective, post-emergence herbicide, it is desirable to carry out treatment in earlier stage of the weed growth. The compounds of formula (I) are also useful as active ingredients for the weed control of vacant lands, reaped fields, and other uncultivated lands.

Of the compounds represented by formula (I), a compound wherein X is $-O-(CH_2CH_2O)_{\overline{n}}R$, particularly compound No. 4, does not show phytotoxicity to wheat, corn, cotton, and soybean plants and has a powerful herbicidal effect on weeds, when used before emergence of weeds, and therefore is particularly useful for these important crops as a pre-emergence herbicide.

For applying the present compounds as a herbicide, they are generally made up, according to the customary procedure for preparing agricultural chemicals, into a form convenient to use. That is, the present compounds are blended with suitable inert carriers and, if necessary, further with adjuvants, in a suitable ratio, and through dissolution, dispersion, suspension, mechanical mixing, impregnation, adsorption, or adhesion, a suitable form of preparation, e.g., suspensions, emulsifiable concentrates, solutions, wettable powders, dusts, granules, or tablets may be obtained.

The inert carriers to be used in the formulations may be either solids or liquids. As examples of the adaptable solid carriers, may be cited vegetable powders such as soybean flour, cereal flour, wood flour, bark flour, saw dust, powdered tobaco stalk, powdered walnut shell, bran, powdered cellulose, and extraction residues of vegetables; fibrous materials such as paper, corrugated paperboard, and waste cloth; synthetic polymers such as powdered synthetic resins; inorganic or mineral products such as clays (e.g., kaolin, bentonite, and acid clay), talcs (e.g., talc and pyrophillite), siliceous substances [e.g., diatomaceous earth, silica sand, mica, and "white carbon" (highly dispersed synthetic silicic acid, also called finely devided hydrated silica or hydrated silicic acid; some commercial products contain calcium silicate as major constituent)], activated carbon, powdered sulfur, pumice, calcined diatomaceous earth, ground brick, fly ash, sand, calcium carbonate, and calcium phosphate; chemical fertilizers such as ammonium sulfate, ammonium nitrate, urea, and ammonium chloride; and farmyard manure. These materials are used separately or in combination. The material usable as liquid carriers are selected from those which are solvents for the active compounds and those which are non-solvent but can disperse the active compounds with the aid of adjuvants. For example, the following materials can be used alone or in combination: water, alcohols (e.g., methanol, ethanol, isopropanol, butanol, ethylene glycol), ketones (e.g., acetone, methyl ethyl ketone, methyl isobutyl ketone, diisobutyl ketone, and cyclohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent napththa, and alkylnapthalenes), halohydrocarbons (e.g., dichloroethane, chlorinated benzenes, chloroform, and carbon tetrachloride), esters (e.g., ethyl acetate, dibutyl phthalate, diisopropyl phthalate, and dioctyl phthalate), acid amides (e.g., dimethylformamide, diethylformamide, and dimethylacetamide), nitriles (e.g., acetonitrile), and dimethyl sulfoxide.

The adjuvants, which are exemplified below, are used according to individual purposes. In some cases, they are used in combination. In some other cases, no adjuvant is used at all.

For the purpose of emulsification, dispersion, solubilization and/or wetting of the active compounds, there are used surface active agents, for example, polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, napththalenesulfonic acid condensation products, ligninsulfonates, and higher alcohol sulfate esters.

For the purpose of stabilizing the dispersion, tackification, and/or agglomeration of the active compounds, may be used, for example, casein, gelatin, starch, alginic acid, methylcellulose, carboxymethylcellulose, gum arabic, polyvinyl alcohol, turpentine oil, rice bran oil, bentonite, and ligninsulfonates.

For the purpose of improving the flow property of the solid compositions, it is recommendable to use waxes, stearates, or alkyl phosphates.

As a peptizer for a dispersible composition, it is also recommendable to use a naphthalenesulfonic acid condensation product on a polyphosphate.

It is also possible to add a defoamer such as, for example, a silicone oil.

The content of the active ingredient may be adjusted as occasion demands; for the preparation of powdered or granulated products, it is usually 0.5 to 20% by weight, and for the preparation of emulsifiable concentrates or wettable powder products, it is desirably 0.1 to 50% by weight.

For destroying various weeds, inhibiting their growth, or protecting useful plants from the injury caused by weeds, a weed-destroying dosage or a weed growth-inhibiting dosage of the present herbicidal composition is applied as such or after properly diluted with or suspended in water or in other suitable medium, to the soil or the foliage of weeds in the area where the emergence or growth of weeds is undesirable.

The amount of the present herbicide to be used depends on various factors such as, for example, the purpose of application, objective weeds, the emergence or growth state of weeds and crops, the seasonal prevalence of weeds, weather, environmental conditions, formulation, application method, the type of the field to be treated, and the time of application.

In applying the present herbicidal composition alone as a selective herbicide, it is suitable to select the dosage of the present active compound from the range of 10 to 500 g per 10 ares. Considering that, in the combined use of herbicides, the optimum dosage thereof is often lower than that in the single use, the present herbicide may be used in an amount lower than the above, when it is used in combination with another sort of herbicide.

The present herbicide is especially valuable for the pre-emergence treatment and initial emergence stage treatment of upland fields and for the early stage and middle stage control of weeds in paddy fields. In order to expand both the range of controllable weed species and the period of time when effective applications are possible or to reduce the dosage, the present herbicides can be used in combination with other herbicides, and this usage is within the scope of this invention. For example, the present herbicide can be used in combination with one or more of the following herbicides: phenoxy fatty acid group herbicides such as 2.4-PA's (e.g., 2,4-dichlorophenoxyacetate), MCP's (e.g., ethyl 2-methyl-4-chlorophenoxyacetate, sodium 2-methyl-4-chlorophenoxyacetate, and allyl 2-methyl-4-chlorophenoxyacetate), MCPB (ethyl 2-methyl-4-chlorophenoxybutyrate); diphenyl ether group herbicides such as NIP (2,4-dichlorophenyl 4'-nitrophenyl ether), CNP (2,4,6-trichlorophenyl 4'-nitrophenyl ether), and Chlomethoxynil (2,4-dichlorophenyl 3'-methoxy-4'-nitrophenyl ether); s-triazine group herbicides such as CAT [2-chloro-4,6-bis(ethylamino)-s-triazine], Prometryne [2-methylthio-4,6-bis(isopropylamino)-s-triazine], and Simetryne [2-methylthio-4,6-bis(ethylamino)-s-triazine]; carbamate group herbicide such as Molinate (S-ethylhexahydro-1H-azepin-1-carbothioate), MCC [methyl N-(3,4-dichlorophenyl) carbamate], IPC [isopropyl N-(3-chlorophenyl) carbamate], Benthiocarb [S-(4-chlorobenzyl)N,N-diethylthiocarbamate]; and other herbicides such as DCPA (3,4-dichloropropionanilide), Butachlor [2-chloro-2',6'-diethyl-N-(butoxymethyl)-acetanilide], Alachlor [2-chloro-2',6'-diethyl-N-(methoxymethyl)acetanilide] and Bentazon [3-isopropyl-2,1,3-benzothiadiazinone-(4)-2,2-dioxide]. The above abbreviations conform to the description in "Pesticide Manual, 1978" published by Japan Plant Protection Association.

The following examples illustrate the process of synthesis, herbicidal effect, and formulations of the compounds of this invention, but the invention is not to be limited to these examples.

SYNTHETIC PROCESS EXAMPLE 1

Synthesis of s-ethyl-2-chloro-5-(2-chloro-4-trifluoromethylphenoxy)benzothioate (compound No. 2)

In 20 ml pyridine was dissolved 0.5 g of ethyl mercaptan, and 2.0 g (0.054 mol) of 2-chloro-5-(2-chloro-4-trifluoromethylphenoxy)benzoyl chloride was gradually added while stirring at room temperature. After 2 hours, the reaction fluid was poured into 200 ml of water and extracted with ether. The extract was well washed with a dilute aqueous solution of caustic soda and with dilute hydrochloric acid, and then dehydrated by adding sodium sulfate. By vacuum concentration thereof 1.7 g (0.045 mol) of the intended product was obtained as an oily substance; yield 83.3%, $_nD_{25}$ 1.5612.

SYNTHETIC PROCESS EXAMPLE 2

Synthesis of methoxyethyl-2-chloro-5-(2-chloro-4-trifluoromethylphenoxy)benzoate (compound No. 4)

In 20 ml methyl cellosolve was heated 2.0 g (0.0054 mol) of 2-chloro-5-(2-chloro-4-trifluoromethylphenoxy)benzoyl chloride to temperatures of 80°–120° C. for 3 hours with stirring. After methyl cellosolve was distilled off, the residue was extracted with benzene. The extract was washed with a dilute aqueous solution of caustic soda and with water, and then dehydrated by adding sodium sulfate. By vacuum concentration thereof 2.2 g (0.0047 mol) of the intended product was obtained as a viscous oily substance; yield 87.0%, $_nD_{25}$ 1.5321.

SYNTHETIC PROCESS EXAMPLE 3

Synthesis of ethoxyethoxyethyl-2-chloro-5-(2-chloro-4-trifluoromethylphenoxy)benzoate (compound No. 10)

In 20 ml pyridine was dissolved 2.0 g (0.0167 mol) of triethylene glycol monoethyl ether, and while stirring at room temperature, 1.8 g (0.0049 mol) of 2-chloro-5-(2-chloro-4-trifluoromethylphenoxy)benzoyl chloride was added. After 4-hour stirring, the reaction fluid was poured into 200 ml of water, and extracted with benzene. The extract was washed with a dilute aqueous solution of caustic soda and then with dilute hydrochloric acid. By concentration 1.4 g (0.0031 mol) of the intended product was obtained as a viscous oily substance, yield 63.3%, $_nD_{28}$ 1.5175.

SYNTHETIC PROCESS EXAMPLE 4

Synthesis of ethylthioethyl-2-chloro-5-(2-chloro-4-trifluoromethylphenoxy)benzoate (compound No. 14)

In 20 ml tetrahydrofuran were dissolved 0.8 g (0.0075 mol) of ethyl thioethanol and 0.8 g (0.0079 mol) of triethylamine, and while heating to 60°–80° C., 1.6 g (0.0043 mol) of 2-chloro-5-(2-chloro-4-trifluoromethylphenoxy)benzoyl chloride was added. After 5-hour stirring, the resulting mixture was cooled, freed of the solvent under reduced pressure, and extracted with benzene. The extract was washed with a dilute aqueous solution of caustic soda and then with dilute hydrochloric acid, and dehydrated with sodiumsulfate. By concentration, 1.0 g (0.0023 mol) of the intended product was obtained as an oily substance; yield 53.0%, $_nD_{23}$ 1.5500.

SYNTHETIC PROCESS EXAMPLE 5

Synthesis of ethoxyethyl-2-chloro-5-(2-chloro-4-trifluoromethylphenoxy)benzoate (compound No. 5)

In 80 ml ethyl cellosolve was dissolved 2.0 g (0.0057 mol) of 2-chloro-5-(2-chloro-4-trifluoromethylphenoxy)benzoic acid, and a catalytic amount of sulfuric acid was added. The mixture was heated to reflux for 8 hours. After stopping of the reaction, ethyl cellosolve was removed by distillation, and the residue was extracted with benzene. The extract was washed with a dilute aqueous solution of caustic soda and then with water, and dehydrated with sodium sulfate. By concentration 1.8 g (0.0037 mol) of the intended product was obtained; yield 65.2%, $_nD_{25}$ 1.5272.

REFERENCE EXAMPLE 1

Synthesis of 2-chloro-5-(2-chloro-4-trifluoromethylphenoxy)benzoyl chloride

In 100 ml sulfonylchloride was heated 20.0 g (0.057 mol) of 2-chloro-5-(2-chloro-4-trifluoromethylphenoxy)benzoic acid to reflux for 1 hour, and then thionylchloride was removed by distillation. By vacuum distillation of the residue, 18.2 g (0.049 mol) of 2-chloro-5-(2-chloro-4-trifluoromethylphenoxy)benzoyl chloride was obtained; yield 86.0%, b.p. 142°–155° C./0.35 mmHg, $n_{D25}$ 1.5652.

REFERENCE EXAMPLE 2

Synthesis of 2-chloro-5-(2-chloro-4-trifluoromethylphenoxy)benzoyl chloride

A mixture of 10.0 g (0.025 mol) of 5-(2-chloro-4-trifluoromethylphenoxy)-2-sulfobenzoic acid with 50 g of phosphorous pentachloride was heated with stirring for 2 hours on an oil bath (180°–220° C.). After completion of the reaction, the excess of phosphorous pentachloride was removed using an evaporator, then the remaining oily matter was vacuum-distilled, and 6.8 g (0.018 mol) of 2-chloro-5-(2-chloro-4-trifluoromethylphenoxy)benzoyl chloride was obtained; yield 72.0%; b.p. 142°–155° C./0.35 mmHg.

TEST EXAMPLE 1

Pots (1/10,000-are) were filled with soil to simulate a paddy field, and planted separately with barnyard grass, monochoria, umbrella plant, bulrush, and Arrowhead, which were conditioned so as to be in a pre-emergence stage. Further, young seedlings of rice plant of 2.5 leaf age were transplanted to the soil on the day before the treatment, which was made by spraying each of the present active compounds formulated to a given concentration of liquid. On 21 days after the treatment, the herbicidal effect on each injurious weed and the degree of chemical injury of the crop were evaluated by comparing with the results of the untreated plot. The judgments were in accordance with the following criteria, respectively:

| Criterion for judging herbicidal effect | |
|---|---|
| Degree of herbicidal effect | Percent control of weed growth (%) |
| 5 | 100 |
| 4 | 90–99 |
| 3 | 80–89 |
| 2 | 70–79 |
| 1 | <70 |

| Criterion for judging degree of chemical injury |
|---|
| H: High (including withering) |
| M: Medium |
| L: Low |
| N: None |

The results are summarized in Table 2.

TABLE 2

| Compound No. | Amount of active ingredient applied (g/are) | Degree of chemical injury | Herbicidal effect | | | | |
|---|---|---|---|---|---|---|---|
| | | | Barnyard grass | Monochoria | Umbrella plant | Bulrush | Arrowhead |
| 1 | 12.5 | L | 5 | 5 | 5 | 5 | 5 |
| | 6.25 | L | 5 | 5 | 5 | 5 | 4 |
| 2 | 12.5 | L | 5 | 5 | 5 | 5 | 4 |
| | 6.25 | L | 5 | 5 | 5 | 4 | 4 |
| 3 | 12.5 | L | 5 | 5 | 5 | 5 | 4 |
| | 6.25 | N | 5 | 5 | 5 | 4 | 4 |
| 4 | 12.5 | L | 5 | 5 | 5 | 5 | 5 |
| | 6.25 | L | 5 | 5 | 5 | 5 | 5 |
| 5 | 12.5 | L | 5 | 5 | 5 | 5 | 5 |
| | 6.25 | L | 5 | 5 | 5 | 5 | 5 |
| 6 | 12.5 | L | 5 | 5 | 5 | 5 | 4 |
| | 6.25 | N | 5 | 5 | 5 | 4 | 4 |
| 7 | 12.5 | L | 5 | 5 | 5 | 5 | 5 |
| | 6.25 | L | 5 | 5 | 5 | 5 | 5 |
| 8 | 12.5 | L | 5 | 5 | 5 | 5 | 5 |
| | 6.25 | L | 5 | 5 | 5 | 4 | 5 |
| 9 | 12.5 | L | 5 | 5 | 5 | 5 | 5 |
| | 6.25 | L | 5 | 5 | 5 | 5 | 5 |
| 10 | 12.5 | L | 5 | 5 | 5 | 5 | 5 |
| | 6.25 | L | 5 | 5 | 5 | 5 | 5 |
| 11 | 12.5 | L | 5 | 5 | 5 | 5 | 5 |
| | 6.25 | N | 5 | 5 | 5 | 4 | 4 |
| 12 | 12.5 | L | 5 | 5 | 5 | 5 | 5 |
| | 6.25 | N | 5 | 5 | 5 | 4 | 4 |
| 13 | 12.5 | L | 5 | 5 | 5 | 5 | 5 |
| | 6.25 | L | 5 | 5 | 5 | 5 | 5 |
| 14 | 12.5 | L | 5 | 5 | 5 | 5 | 5 |
| | 6.25 | L | 5 | 5 | 5 | 5 | 4 |
| 15 | 12.5 | L | 5 | 5 | 5 | 5 | 4 |
| | 6.25 | L | 5 | 5 | 5 | 4 | 4 |
| Note (1) A | 12.5 | L | 5 | 5 | 5 | 3 | 3 |
| | 6.25 | L | 4 | 4 | 4 | 2 | 2 |

Note (1) Isopropyl-2-chloro-5-(2-chloro-4-trifluoromethylphenoxy)benzoate

TEST EXAMPLE 2

Pots (1/10,000are) were filled with soil to simulate a paddy field and grown with each of injurious weeds of the following leaf ages. Then, the weeds were treated by spraying with each of the present active compounds formulated to a given concentration of liquid. On 21 days after the treatment, each herbicidal effect was evaluated by comparing with the results of the untreated plot. The results are summarized in Table 3.

The criterion for judging the herbicidal effect is in accordance with Test Example 1.

| Species of sample weed | Leaf age of weed |
|---|---|
| Barnyard grass | 1 |
| Monochoria | 2–3 |
| Umbrella plant | 2–3 |
| Bulrush | 2–3 |
| Arrowhead | 3 |

TABLE 3

| Compound No. | Amount of active ingredient applied (g/are) | Herbicidal effect | | | | |
|---|---|---|---|---|---|---|
| | | Barnyard grass | Monochoria | Umbrella plant | Bulrush | Arrowhead |
| 1 | 25 | 5 | 5 | 5 | 5 | 4 |
| | 12.5 | 5 | 5 | 4 | 4 | 4 |
| 2 | 25 | 5 | 5 | 4 | 4 | 4 |
| | 12.5 | 5 | 5 | 4 | 4 | 3 |
| 4 | 25 | 5 | 5 | 5 | 5 | 5 |
| | 12.5 | 5 | 5 | 5 | 4 | 4 |
| 5 | 25 | 5 | 5 | 5 | 5 | 4 |
| | 12.5 | 5 | 5 | 5 | 4 | 4 |
| 6 | 25 | 5 | 5 | 5 | 4 | 4 |

TABLE 3-continued

| Compound No. | Amount of active ingredient applied (g/are) | Herbicidal effect | | | | |
|---|---|---|---|---|---|---|
| | | Barnyard grass | Monochoria | Umbrella plant | Bulrush | Arrowhead |
| | 12.5 | 5 | 5 | 4 | 4 | 3 |
| 7 | 25 | 5 | 5 | 5 | 5 | 4 |
| | 12.5 | 5 | 5 | 4 | 4 | 4 |
| 8 | 25 | 5 | 5 | 5 | 4 | 5 |
| | 12.5 | 5 | 5 | 4 | 3 | 4 |
| 9 | 25 | 5 | 5 | 5 | 5 | 4 |
| | 12.5 | 5 | 5 | 5 | 4 | 4 |
| 10 | 25 | 5 | 5 | 5 | 4 | 4 |
| | 12.5 | 5 | 5 | 4 | 4 | 3 |
| 11 | 25 | 5 | 5 | 5 | 5 | 4 |
| | 12.5 | 5 | 5 | 4 | 4 | 4 |
| 13 | 25 | 5 | 5 | 5 | 5 | 4 |
| | 12.5 | 5 | 5 | 4 | 4 | 4 |
| 14 | 25 | 5 | 5 | 5 | 5 | 4 |
| | 12.5 | 4 | 5 | 4 | 4 | 4 |
| Note (1) A | 25 | 4 | 4 | 4 | 3 | 3 |
| | 12.5 | 3 | 3 | 3 | 2 | 2 |
| Note (2) B | 20 | 5 | 3 | 3 | 2 | 1 |
| Note (3) C | 25 | 4 | 4 | 4 | 3 | 3 |
| | 12.5 | 3 | 3 | 3 | 2 | 2 |

Note (1) Isopropyl-2-chloro-5-(2-chloro-4-trifluoromethylphenoxy)benzoate
Note (2) A commercial herbicide, 2,4-dichlorophenyl-4-nitrophenyl ether
Note (3) A commercial herbicide, 2,4-dichlorophenyl-3'-methoxy-4'-nitrophenyl ether

TEST EXAMPLE 3

Polyethylene vats, 10 cm×20 cm×5 cm (depth), were filled with soil and seeded in rows with barnyard grass, large crabgrass, redroot pigweed, mugwort, and umbrella sedge, separately. The seeds were covered with soil depth of 1 cm, and before emergence of each weed, each of the present active compounds formulated to a given concentration of liquid was sprayed uniformly onto the soil surface of the soil. On 21 days after the treatment, each herbicidal effect was evaluated by comparing with the results of the untreated plot.

The results are summarized in Table 4. The criterion for judging the herbicidal effect is in accordance with Test Example 1.

TABLE 4

| Compound No. | Amount of active ingredient applied (g/are) | Herbicidal effect | | | | |
|---|---|---|---|---|---|---|
| | | Barnyard grass | Large crabgrass | Redroot pigweed | Mugwort | Umbrella sedge |
| 1 | 25 | 5 | 5 | 5 | 5 | 5 |
| | 12.5 | 5 | 5 | 5 | 5 | 5 |
| 2 | 25 | 5 | 5 | 5 | 5 | 5 |
| | 12.5 | 4 | 5 | 5 | 5 | 5 |
| 3 | 25 | 5 | 5 | 5 | 5 | 5 |
| | 12.5 | 4 | 4 | 5 | 5 | 5 |
| 4 | 25 | 5 | 5 | 5 | 5 | 5 |
| | 12.5 | 5 | 5 | 5 | 5 | 5 |
| 5 | 25 | 5 | 5 | 5 | 5 | 5 |
| | 12.5 | 4 | 5 | 5 | 5 | 5 |
| 6 | 25 | 5 | 5 | 5 | 5 | 5 |
| | 12.5 | 5 | 5 | 5 | 5 | 5 |
| 7 | 25 | 5 | 4 | 5 | 5 | 5 |
| | 12.5 | 5 | 5 | 5 | 5 | 5 |
| 11 | 25 | 5 | 5 | 5 | 5 | 5 |
| | 12.5 | 4 | 5 | 5 | 5 | 5 |
| 12 | 25 | 5 | 5 | 5 | 5 | 5 |
| | 12.5 | 4 | 5 | 5 | 5 | 5 |

EXAMPLE 1

A wettable powder composition obtained by uniformly mixing and grinding the following constituents:

| Compound No. 4 | 50 parts |
|---|---|
| Mixture of clay and white carbon (clay is the major constituent) | 45 parts |
| Polyoxyethylene nonylphenyl ether | 5 parts |

EXAMPLE 2

A granule composition obtained by uniformly mixing and grinding the following constituents, kneading the mixture with a suitable amount of water, and granulating the kneaded mixture:

| Compound No. 6 | 5 parts |
|---|---|
| Mixture of bentonite and clay | 90 parts |
| Calcium liguninsulfonate | 5 parts |

EXAMPLE 3

An emulsifiable concentrate obtained by uniformly mixing the following constituents:

| Compound No. 8 | 50 parts |
|---|---|
| Xylene | 40 parts |
| Mixture of polyoxyethylene nonylphenyl ether and calcium alkylbenzenesulfonate | 10 parts |

In the above Examples, "parts" means parts by weight.

What is claimed is:

1. Benzoate derivative represented by the formula

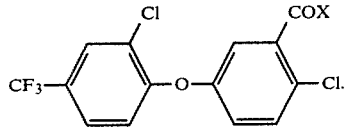

wherein X is —SR, —O—(CH₂CH₂O)ₙR, —OCH₂CH₂SR,

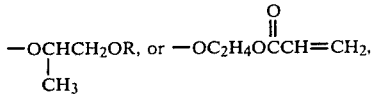

herein R being lower alkyl and n being an integer of 1 to 3.

2. Benzoate derivative of claim 1, wherein X is —O—(CH₂CH₂O)ₙR, herein R being lower alkyl and n being an integer of 1 to 3.

3. Benzoate derivative of claim 2, wherein n is 1.

4. Benzoate derivative of claim 2, wherein R is methyl.

5. Benzoate derivative of claims, wherein said benzoate derivative ismethoxyethyl-2-chloro-5-(2-chloro-4-trifluoromethylphenoxy)benzoate.

6. A herbicidal composition comprising an effective amount of a benzoate derivative represented by the formula

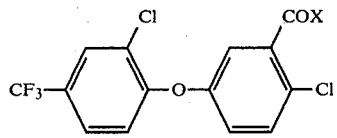

wherein X is —SR, —O—(CH₂CH₂O)ₙR, —OCH₂CH₂SR,

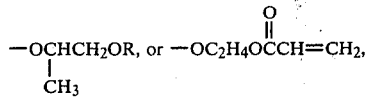

herein R being lower alkyl and n being an integer of 1 to 3 and an inert diluent.

7. A herbicidal composition of claim 6, wherein said benzoate derivative is methoxyethyl-2-chloro-5-(2-chloro-4-trifluoromethylphenoxy)benzoate.

8. Benzoate derivative according to claim 1 where X is —OCH₂CH₂SR.

9. Benzoate derivative according to claim 1 where X is

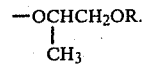

10. Benzoate derivative according to claim 1 where X is

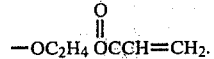

11. Benzoate derivative according to claim 1 where X is —SR.

12. A process of at least inhibiting the growth of weeds comprising applying a dosage of a compound of claim 1 effective for such purpose.

13. A process according to claim 12 wherein X is —O—(CH₂CH₂O)ₙR.

14. A process according to claim 13 where n is 1.

15. A process according to claim 14 where R is methyl.

16. A process according to claim 15 wherein the benzoate derivative is methoxyethyl-2-chloro-5-(2-chloro-4-trifluoromethyl)-phenoxy-benzoate.